(12) United States Patent
Klettke et al.

(10) Patent No.: US 8,022,113 B2
(45) Date of Patent: Sep. 20, 2011

(54) COMPOSITION CONTAINING AZIRIDINO GROUPS AND USE THEREOF

(75) Inventors: Thomas Klettke, Diessen (DE); Cornelia B. Fuehrer, Wertach (DE); Peter Bissinger, Diessen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 316 days.

(21) Appl. No.: 12/278,983

(22) PCT Filed: Feb. 8, 2007

(86) PCT No.: PCT/US2007/003389
§ 371 (c)(1),
(2), (4) Date: Aug. 11, 2008

(87) PCT Pub. No.: WO2007/097921
PCT Pub. Date: Aug. 30, 2007

(65) Prior Publication Data
US 2009/0068619 A1    Mar. 12, 2009

(30) Foreign Application Priority Data

Feb. 15, 2006  (EP) .................................... 06003085

(51) Int. Cl.
*A61K 6/10* (2006.01)
*A61C 9/00* (2006.01)
*C08C 19/22* (2006.01)

(52) U.S. Cl. .......................... 523/109; 433/214; 525/375

(58) Field of Classification Search .................. 523/109; 433/214; 525/375
See application file for complete search history.

(56) References Cited

U.S. PATENT DOCUMENTS

| | | | |
|---|---|---|---|
| 3,453,242 A | 7/1969 | Schmitt et al. | |
| 3,634,400 A | 1/1972 | Schmitt et al. | |
| 4,167,618 A | 9/1979 | Schmitt et al. | |
| 4,605,698 A | 8/1986 | Briden | |
| 5,130,348 A | 7/1992 | Zahler et al. | |
| 5,164,467 A | 11/1992 | Kania | |
| 5,401,505 A * | 3/1995 | Duell et al. ................... | 424/408 |
| 5,569,691 A | 10/1996 | Guggenberger et al. | |
| 6,063,286 A | 5/2000 | Steuerle et al. | |
| 6,127,449 A | 10/2000 | Bissinger et al. | |
| 6,383,279 B1 | 5/2002 | Eckhardt et al. | |
| 6,656,889 B2 | 12/2003 | Eichenauer | |
| 6,906,117 B2 | 6/2005 | Nowak et al. | |
| 6,919,386 B2 | 7/2005 | Wanek et al. | |
| 7,053,135 B2 | 5/2006 | Schaub et al. | |
| 7,276,545 B2 * | 10/2007 | Eckhardt et al. .............. | 523/109 |
| 7,504,442 B2 | 3/2009 | Bublewitz et al. | |
| 2004/0014907 A1 | 1/2004 | Nowak et al. | |
| 2004/0014924 A1 | 1/2004 | Nowak et al. | |
| 2006/0106127 A1 | 5/2006 | Klettke et al. | |

FOREIGN PATENT DOCUMENTS

| | | |
|---|---|---|
| DE | 116471 | 3/1964 |
| DE | 15 44 837 | 4/1970 |
| DE | 3728216 | 3/1988 |
| DE | 197 53 456 | 6/1999 |
| DE | 10026857 A1 | 12/2001 |
| DE | 10235990 | 2/2004 |
| EP | 0 110 429 | 6/1984 |
| EP | 0 421 371 | 4/1991 |
| EP | 1 748 057 | 1/2007 |
| WO | WO 85/02873 | 7/1985 |
| WO | WO 92/19655 A1 | 11/1992 |
| WO | WO 98/53791 A2 | 12/1998 |
| WO | WO 01/52792 | 7/2001 |
| WO | WO 02/043670 | 7/2002 |
| WO | WO 2004/014323 A1 | 2/2004 |

OTHER PUBLICATIONS

Roesler et al., TRIS-3-(1-Aziridino) Propionates and Their Use in Formulated Products, Prog Org Coatings, Progress in Organic Coatings, Jun. 2004, vol. 50, No. 1, pp. 1-27.
Search Report for PCT/US2007/003389.
Search Report for PCT/US2007/070057.
DIN-53504.
DIN-53505.

* cited by examiner

*Primary Examiner* — Tae H Yoon
(74) *Attorney, Agent, or Firm* — Pamela L. Stewart

(57) ABSTRACT

The invention relates to a composition comprising a prepolymer as component (A), wherein the prepolymer comprises aziridino groups and is characterized by an equivalent weight EW1, a crosslinker as component (B), wherein the crosslinker has a structure being different from the structure of the prepolymer and comprises aziridino groups and is characterized by an equivalent weight EW2, an initiator as component (C) being able to start curing of the composition, optionally filler(s) as component (D) and optionally additive(s) as component (E), wherein equivalent weight is defined as (molecular mass of the molecule)/(number of aziridino groups present in the molecule) and wherein EW1>EW2. The invention also relates to the use of the composition for coating, sealing, moulding, adhering, making impressions, producing a dental material.

13 Claims, No Drawings

US 8,022,113 B2

COMPOSITION CONTAINING AZIRIDINO GROUPS AND USE THEREOF

CROSS REFERENCE TO RELATED APPLICATIONS

This application is a national stage filing under 35 U.S.C. 371 of PCT/US2007/003389, filed Feb. 8, 2007, which claims priority to European Application No. 06003085.5, filed Feb. 15, 2006, the disclosure of which is incorporated by reference in its/their entirety herein.

FIELD

The invention relates to a composition comprising a prepolymer with aziridino groups as component (A), a crosslinker with aziridino groups as component (B) and an initiator being able to start curing the composition as component (C). The composition is especially useful in the dental field, e.g. as dental impression material.

BACKGROUND

Due to their chemical nature, polyethers are inherently hydrophilic and are a well-recognized class of materials, especially for dental applications. Polyether-containing compositions and their use in the dental field are also subject of several patent applications.

US 2004/0014924 A1 relates to silicone based aziridino compounds. The materials described show functionality of at least two aziridino groups in the average molecule having a prepolymeric structure. The general formula shows structures with aziridino functions pendant from a silicone backbone.

US 2004/0014907 A1 describes linear and branched prepolymeric silicones bearing terminal and/or pendant aziridino moieties and curable compositions made thereof.

WO 2004/014323 A1 relates to monofunctional aziridine compounds which can be used to enhance speed of cure. The addition of monofunctional aziridine compounds to a given concentration of aziridine compounds with at least two aziridine rings enhances speed of cure.

Other publications that mention the use of aziridines are WO 92/19655 A1, U.S. Pat. No. 5,164,467 A1 and U.S. Pat. No. 4,605,698 A1.

So far achieving a sufficient tear strength value of the compositions described has not been an issue. Some of the compositions, however, might lack sufficient tear strength bearing the risk of rupture of thin parts of material when the set impression is removed from the mouth or a plaster model is removed from the impression.

Thus, there is a need for a polyether containing composition having improved properties, especially with regard to tear strength.

SUMMARY OF THE INVENTION

It might be advantageous if an improved tear strength value can be achieved by simply adding an additive being able to modify the network structure rather than developing an entirely new formulation. However, simply adding further components to an existing composition might cause other drawbacks in view of the fact that compositions containing aziridino groups cure in a quite complex manner. For example, in aziridino polymerization, ring formation of di- and oligomerization is a well known side reaction which becomes pronounced with high functional group density (Encyclopedia of Polymer Science and Engineering Vol. 1, p 698ff, Wiley 1985 ISBN: 0-471-89540-7 (v.1)).

Commercially available trifunctional aziridino monomers like TTMAP, TTAP or PTAP (R. R. Roesler, K. Danielmeier, Progress in Organic Coatings 50 (2004) 1-27) on the one hand might be highly functional and have a low aziridino equivalent. On the other hand, however, these substances have very low molecular weights which can result in insufficient crosslinking because of the high functional density of these substances.

Moreover, simply increasing the aziridino functionality of some of the components of the composition combined with an appropriate alteration of the initiating system often results in a more or less significant acceleration of cure.

In the dental field the curing behaviour of impression materials is characterized by the working time and the setting time. The working time is defined according to DIN EN ISO 4823:2000. The setting time is defined as the time until the cured elastomer shows a recovery after deformation of at least 96.5% as measured according to DIN EN ISO 4823:2000 and a strain in compression within the limits of DIN EN ISO 4823:2000.

While a reduced setting time alone would be rather desirable, acceleration often is accompanied with a shortened working time, which may be unsuitable for certain dental procedures.

In one aspect, the invention provides a curable composition comprising aziridino groups with improved mechanical properties, especially in regard to tear strength.

In some implementations of the invention, it might be advantageous if this improved tear strength can be achieved without a negative effect on other physical properties such as e.g. Shore hardness or a decrease of other elastomeric properties, such as elongation at break.

In one embodiment, the invention features a composition comprising:
a) a prepolymer as component (A), wherein the prepolymer comprises aziridino groups and is characterized by an equivalent weight EW1,
b) a crosslinker as component (B), wherein the crosslinker has a molecular structure being different from the structure of the prepolymer and comprises aziridino groups and is characterized by an equivalent weight EW2,
c) an initiator as component (C) being able to start curing of the composition,
d) optionally filler(s) as component (D) and
e) optionally additive(s) as component (E),
wherein equivalent weight EW is defined as (molecular mass of the molecule)/(number of aziridino groups present in the molecule) and wherein EW1>EW2.

The invention also relates to a kit of parts comprising
Part I comprising component (A) and component (B) and optionally component (D) and/or component (E) and
Part II comprising component (C) and optionally component (D) and/or component (E).

Moreover, the invention relates to a process for producing the composition comprising the step of mixing component (C) with components (A) and (B).

In addition the invention also relates to the use of the composition for coating, sealing, moulding, adhering, making impressions or producing a dental material.

Furthermore, the invention relates to the use of component (B) for increasing the tear strength and/or elongation at break of a polyether containing composition.

DEFINITIONS

A "prepolymer" in the context of the invention is defined as a compound or a mixture of compounds obtainable by polymerization (such as e.g. polycondensation reaction) of monomers resulting in an intermediate product or mixture of products with increased molecular weight compared to the monomers used. The resulting intermediate product itself bears functional groups (either left over from the initial polymerization or introduced afterwards). The prepolymer containing functional groups can be used for further polymerization reactions (such as e.g. polycondensation reaction or polyaddition reaction) leading to a polymer or polymer mixture with increased molecular weight compared to the prepolymer.

The term "crosslinker" refers to compounds being able to react with the functional group or groups on other compounds, prepolymers or polymer chains to lengthen them and connect them, e.g., to form a crosslinked network characteristic like that of a cured silicone elastomer. In contrast to a thermoplastic polymer, (i.e., a polymer that softens and flows upon heating) a crosslinked polymer, after crosslinking, is usually incapable of further flow. Cross-linked polymers differ in some important respects from linear and branched polymers. For example they swell in good solvents to form a gel but do not dissolve to form a solution. At elevated temperature, cross-linked polymers behave like soft but elastic solids rather than viscous liquids.

"Equivalent weight" (EW) in the context of the invention is defined as (EW)=(molecular weight of the respective molecule)/(number of aziridino groups in the molecule).

The equivalent weight reflects the "density" of aziridino groups in the respective molecule.

The lower the value of EW, the more aziridino groups are present in the molecule. The aziridino groups present in component (A) take part in the crosslinking reaction with crosslinker component (B).

For molecules having a low molecular weight the number of aziridino groups can be counted. For molecules having a higher molecular weight the equivalent weight (EW) can be determined by titration of the aziridino groups and determination of the molecular weight of the respective molecule, prepolymer or polymer.

"Molecular weight" in the context of the invention and if not otherwise indicated always means number average molecular weight ($M_n$).

The molecular weight ($M_n$) of the polymerizable compound before setting can be determined with GPC. Appropriate methods are know by the expert.

In addition, the molecular weight can be determined using nuclear magnetic resonance spectroscopy (end-group determination). There are also applicable methods described in the literature for organic polyols that may be used like determination of hydroxyl number according to Houben-Weyl, "Methoden der organischen Chemie", 14/2, page 17, Georg Thieme Verlag, Stuttgart, 1963 or according to ASTM D2849 Method C.

"Polyethers" in the context of the invention are compounds having a molecular weight of at least about 500 and containing in the backbone at least about 5 ether moieties. Polyethers are frequently used in the dental field as impression materials. Polyether containing compositions used as dental impression material can be cured by different mechanisms. Widely used is curing caused by the reaction of aziridino groups with each other.

The term "dental materials" comprises impression materials, such as precision impression materials, situation impression materials, bite registration materials, duplicating materials (applicable for the duplication of master models, e.g. for all-ceramic restorations requiring a refractory investment model and when inlays, onlays, cantilevers and other precision attachments are being fabricated) and modelling materials (applicable for e.g. reconstructing the gingival, producing crowns and bridges). Duplicating and modelling materials are commercially available e.g. from 3M ESPE AG under the trademarks Reprogum™ or Vestogum™.

The terms "comprises" and variations thereof do not have a limiting meaning where these terms appear in the description and claims.

As used herein, "a", "an", "the", "at least one" and "one or more" are used interchangeably. Thus, for example, a dental composition that comprises "a" aziridine group containing prepolymer can be interpreted to mean that the prepolymer includes "one or more" aziridine groups. Similarly, a composition comprising "a" filler can be interpreted to mean that the composition includes "one or more" types of fillers.

Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION

The invention provides a means for improving mechanical properties like tear strength and/or elongation at break of polyether containing impression materials.

It was found that the addition of certain crosslinkers comprising aziridino groups to prepolymers with aziridino groups in the presence of a suitable initiator results in a composition with improved tear strength compared to a composition not containing these crosslinkers.

In addition, besides an improved tear strength value the inventive composition preferably has an improved elongation at break value.

If the set composition has a high elongation at break value, tear strength is not the only property to avoid ruptures of thin parts of material. The higher the value of elongation at break is, the lower is the risk of a rupture of thin parts of material.

For some applications a high hardness can be desirable. For precision impression materials hardness can be important when used with a dental tray that does not support the material. Commonly used trays not supporting the impression material are e.g. dual arch trays. In addition bite registration materials sometimes also should have a high hardness. Hardness is commonly measured as Shore hardness A. A Shore hardness A value of about 45 after 24 h is often considered as sufficient.

In a preferred embodiment the Shore hardness A value of the set composition of the invention is not negatively influenced by the addition of a crosslinker.

In another embodiment the inventive composition sometimes shows improved handling properties of the unset formulation (e.g. with regard to viscosity), thus providing benefits for the dentist when the material is applied e.g. in a syringe.

In one embodiment the prepolymer can be characterized by at least one of the following features:
Molecular weight
Molecular structure
Number of aziridino groups
Equivalent weight (EW1).

The molecular weight of the prepolymer usually is in the range of about 3,000 to about 12,000 or in the range of about 4,000 to about 10,000, or in the range of about 5,000 to about 8,000.

The prepolymer preferably has a linear molecular structure. The prepolymer preferably comprises a linear backbone, which preferably is end-capped with aziridino groups. Usually, there are no side chains pending from the backbone.

The prepolymer usually has an equivalent weight (EW1) of at least about 1,000 preferably of at least about 3,000 or at least about 5,000.

The equivalent weight (EW1) usually does not exceed values of about 6,000 or about 10,000 or about 15,000.

Depending on the chemical nature and structure of the prepolymers chosen, different ranges for EW1 can be preferred.

Suitable ranges for EW1 are e.g. about 1,500 to about 4,000 or about 4,000 to about 10,000 or about 10,000 to about 15,000.

The prepolmyer can comprise at least about 2, 3, 4, 5 or 6 aziridino groups.

The prepolymer can be used in an amount of at least about 30 wt.-% or at least about 35 wt.-% or at least about 40 wt.-% with respect to the whole composition.

The prepolymer can be used up to an amount of at least about 80 wt.-% or at least about 75 wt.-% or at least about 70 wt.-% with respect to the whole composition.

Especially N-alkyl aziridine polyether containing compounds can be used and vulcanized in the presence of the initiator. The aziridine groups containing compound comprises at least two ethylene imine groups. However, more than two aziridine groups can be present, if desired.

Those components are know and described e.g. in U.S. Pat. No. 3,453,242 or U.S. Pat. No. 5,569,691 or U.S. Pat. No. 6,383,279 B1. These documents, especially as regards their disclosure on aziridine groups containing compounds is explicitly mentioned and herewith incorporated by reference.

The aziridine groups can be attached to an oligomeric and/or polymeric hydrocarbon, ester or ether backbone. The attached aziridine group can be represented by the formula

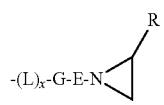

wherein
R represents H, $C_1$-$C_{12}$ alkyl, $C_2$-$C_{12}$ alkenyl, $C_2$-$C_{12}$ alkinyl, $C_7$-$C_{15}$ alkylaryl, $C_7$-$C_{15}$ arylalkyl or $C_3$-$C_{12}$ cycloalkyl, and wherein hydrogen atoms can be replaced by Cl or F and/or wherein up to about 5 carbon atoms may be replaced by atoms or group of atoms selected from O, CO, N or S, E represents a $C_1$-$C_{18}$ branched or unbranched hydrocarbon chain wherein up to about 5 carbon atoms can be replaced by atoms or group of atoms selected from O, CO, N or S, G represents a group selected from C(O)O, C(O)NR, C(O) or C(O)C(O), C(O)($CH_2$)$_m$C(O), with m=1 to 10, C(S)NR or $CH_2$, L represents O, S or NR, with x=0 or 1.

In a preferred embodiment the prepolymer according to the invention does not contain silicone moieties.

In another embodiment the crosslinker can be characterized by at least one of the following features:
Molecular weight
Molecular structure
Number of aziridino groups
Equivalent weight (EW2).

The molecular weight of the crosslinker is usually in the range of about 400 to about 10,000 or in the range of about 1,000 to about 4,000 or in a range of about 2,000 to about 8,000.

A certain molecular weight can be advantageous to reduce functional density of reactive groups in order to ensure a high degree of conversion.

A molecular weight in excess of 1,000 can be advantageous in terms of sensory perception as a high molecular weight reduces undesirable taste of such ingredients.

Low polarity and especially low water solubility can be advantageous, too, both for high degree of conversion and sensory properties. In this respect it can be desirable to use defined structures or mixtures of those rather than prepolymerically distributed mixtures of monomers. The latter often comprise a certain content of rather low molecular constituents that might have high polarity and high water solubility although overall molecular weight is well above 1,000. High molecular weight together with the desired multifunctionality is limited by considerations as regards stability and viscosity of the compound.

The crosslinker has a molecular structure being different from the molecular structure of the prepolymer. The crosslinker usually does not have a linear structure, but a branched structure, i.e. the crosslinker can comprise a backbone with side chains, some of the side chains bearing aziridino groups. The crosslinker molecules are preferably defined molecules or simple mixtures of those but not prepolymeric distributed mixtures.

The backbone can comprise hydrophobic elements such as linear or branched aliphatic or cyclo aliphatic moieties (e.g. $C_2$ to $C_{12}$ moieties) and/or silicone moieties (linear, branched or cyclic). The backbone, however, can comprise hydrophilic elements such as ether or polyethers, as well.

The crosslinker comprises at least about 2, 3, 4, 5, 6, 7, 8, 9 or 10 aziridino groups.

The crosslinker usually has an equivalent weight (EW2) of at least about 100, preferably of at least about 125 or at least about 150.

The equivalent weight (EW2) usually does not exceed values of about 500 or about 800 or about 1,300.

Depending on the chemical nature and structure of the crosslinker chosen, different ranges for EW2 can be preferred.

Suitable ranges for EW2 are e.g. about 100 to about 500 or about 125 to about 900 or about 500 to about 1,300.

The crosslinker can be used in an amount of at least about 0.1 wt.-% or at least about 0.5 wt.-% or at least about 1 wt.-% with respect to the whole composition.

The crosslinker can be used up to an amount of at least about 20 wt.-% or at least about 15 wt.-% or at least about 10 wt.-% with respect to the whole composition.

The aziridino crosslinkers can by synthesized by adding several aziridino functions to a molecular backbone. This can be done by various chemical procedures.

One way is e.g. to add aziridine to the double bonds of polyfunctional acrylates.

Another way is to use polyvalent alcohols or amines. These can be transformed into chloro oxalates or chloro formiates which can be reacted with protic aziridino derivatives like e.g. aziridino ethanol (Acros) or other hydroxy- and amino functional aziridino derivatives.

In some cases it can be preferred to use activated amides as intermediates like imidazolides.

There are numerous other methods known to the persons skilled in the art that are described for instances in: R. C. Elderfield, "Heterocyclic Compounds" Vol. 1. S.61-77 Wiley 1950; Houben-Weyl "Methoden der Organischen Chemie", Bd. XI/2 S.223-264, Thieme 1958; O. C. Dermer, G. E. Ham, "Ethylenimine and other Aziridines" therein especially S. 106-205 as well as S. 340-393, Academic Press 1969; Houben-Weyl "Methoden der Organischen Chemie", Bd. E16c S.370-667, Thieme 1992; Ulmanns Encyclopedia of Industrial Chemistry 5th Ed. Vol. A3 S. 239-243 or R. R. Roesler, K. Danielmeier "Progress in Organic Coatings" 50 (2004) 1-27.

As starting material a molecular backbone can be used comprising a multitude of at least two hydroxy- or primary or secondary amino functions that are available for acylation. The molecular backbone can be taken from a wide variation depending on how introduction of aziridino groups should be facilitated. Among such backbones the following are preferred:

- Silicones backbones can be particular useful, preferably functional derivatives of $D_4$, $D_5$, $D_6$, $M_4Q$, $M_3T$, $D_2$; functional derivatives are e.g. carbinols or carbamines; the terms "$D_4$, $D_5$, $D_6$, $M_4Q$, $M_3T$, $D_2$" are well known terms to the skilled person in the art working in the field of silicones.
- Organic backbones, preferably aliphatic like glycerol, trimethylol ethane or—propane, pentaerythrol or the corresponding dimers via ether bridge, linear or cyclic sugar alcohols like erythrole, sorbitole, mannitol or innositol, aliphatic polyvalent primary or secondary amines like etylene diamine derivatives, piperazine, tris-(aminoethyl) amine derivatives.

To these backbones aziridino functions are connected via acyl groups. The acyl groups can be part of carbonic ester, carbonic amide, carbonate, carbamate or urea groups.

The carbonic esters and amides, which can be used, comprise aliphatic acids ranging from acetic up to undecanoic acids, covering the readily available isomers of the intermediate chain lengths. The aziridino function there is usually attached by addition of an NH or OH moiety on an activated double bond or by substitution of a halide substituent.

The aziridino function can be attached to the acyl function using the aziridino functional compounds found in literature like

 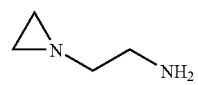

Ethylene imine, Aziridine   2-Aminoethyl ethylene imine

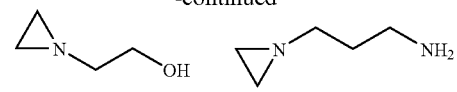

2-Hydroxyethyl ethylene imine   3-Aminoproyl ethylene imine

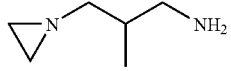

3-Amino-2-methylpropyl ethylene imine

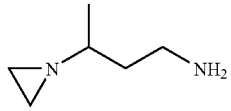

3-Amino-1-methylpropyl ethylene imine

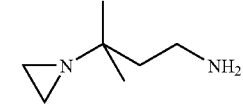

3-Amino-1,1-dimethylpropyl ethylene imine

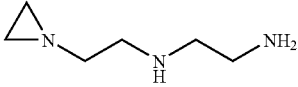

5-Amino-3-azapentyl ethylene imine

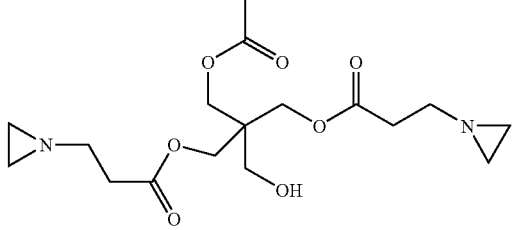

XAMA-7
Functionality = 3; (EW) = 142; m = 427

Suitable crosslinkers are e.g.:
Compound 1:

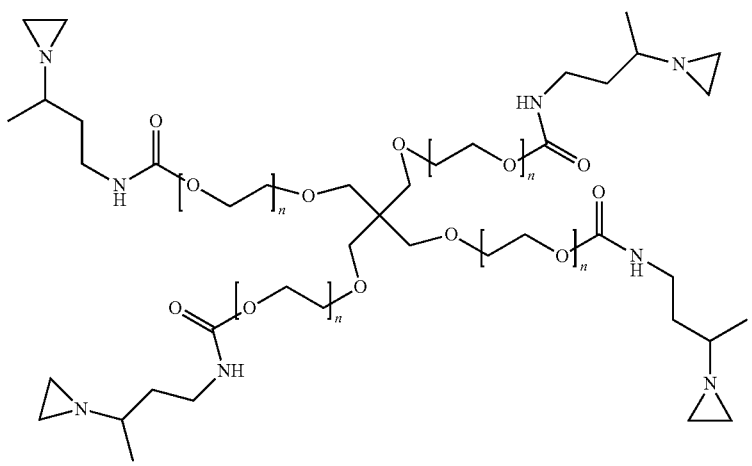

n=2–30 or 5 to 10; Mn=e.g. 2000; Functionality=4; (EW2)= e.g. 486
Compound 2:
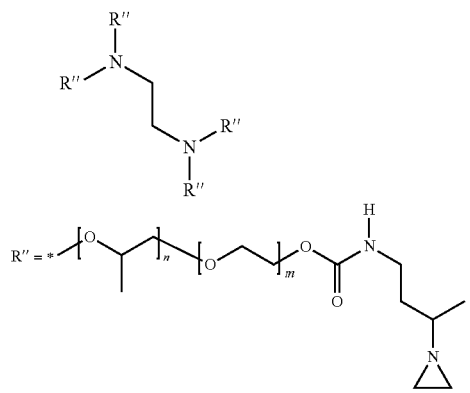
n=2–30 or 5 to 10; m=2–30 or 5 to 10; Mn=e.g. 4684; Functionality=m=4; (EW2) e.g. 1171
Compound 3:
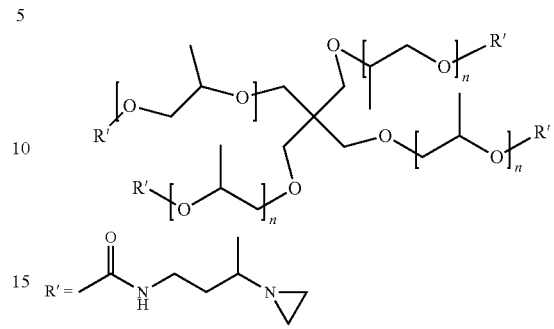
n=2–30 or 5–10; Mn=e.g. 4200; Functionality=4; (EW2)= e.g. 1050
Compound 4:
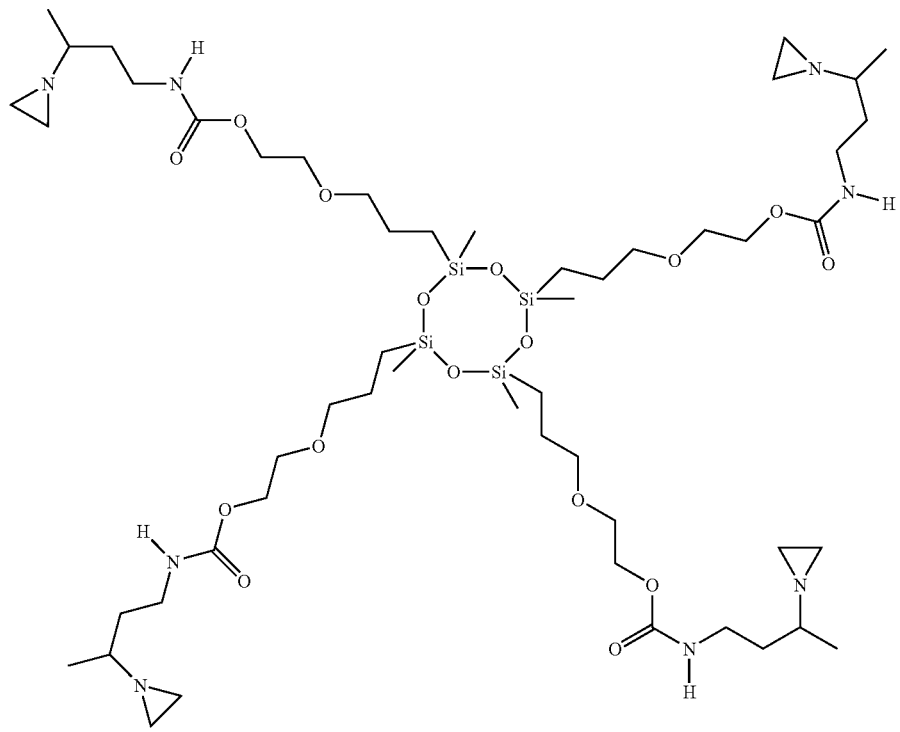
M=1210; Functionality=4; (EW2)=303;
Compound 5:
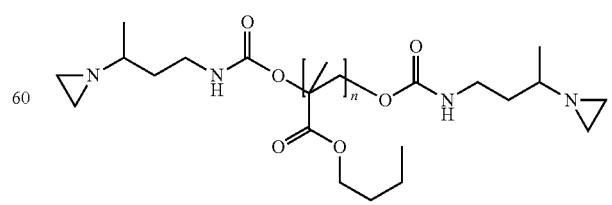
n=5–20 or 8–15; Mn=e.g. 1676; Functionality=2; (EW2)= e.g. 838

Compound 6:
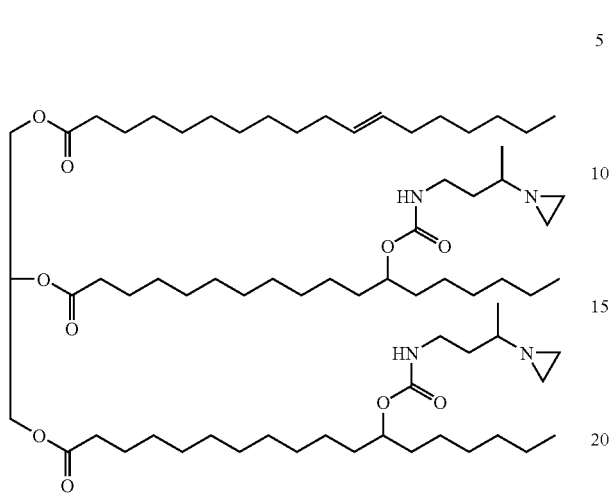
M=1363; Functionality=2; (EW2)=683
Compound 7:
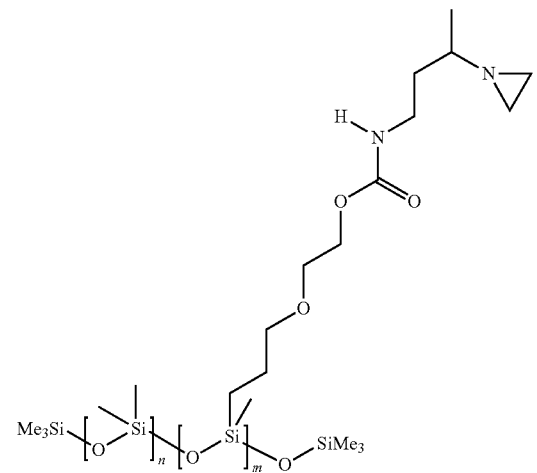
n=5–100 or 10–50 or 15–30; m=3–30 or 5–25 or 10–20;
Mn=e.g. 10,000 (EW2)=e.g. 593
Compound 8
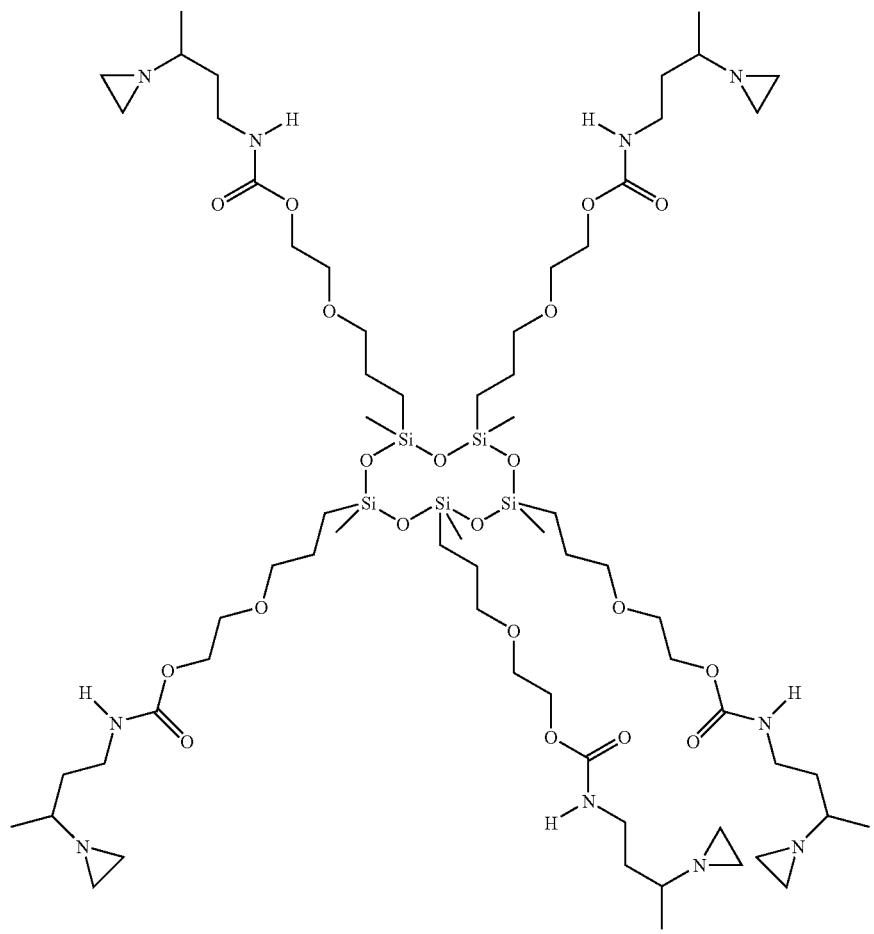

Mw=1512; Functionality=5; (EW2)=303
Compound 9
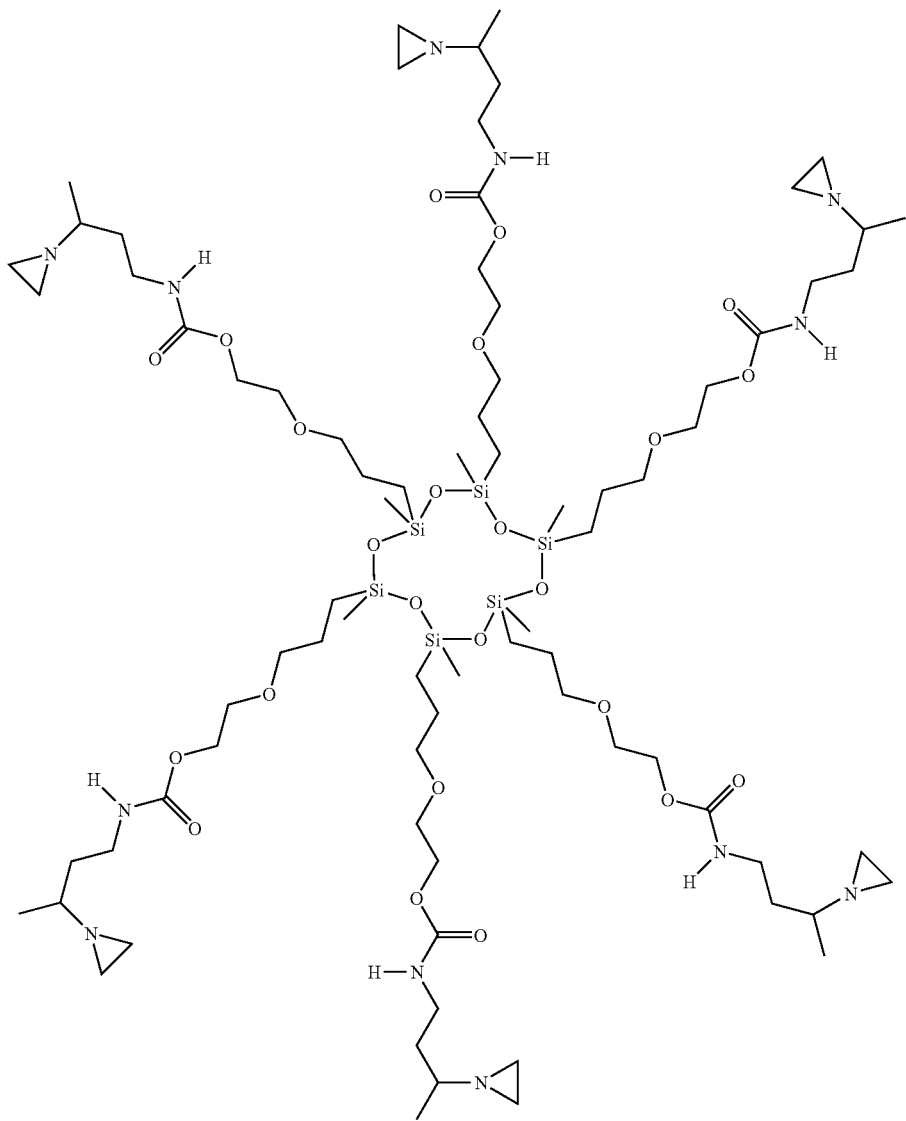
M=1815; Functionality=6; (EW2)=303
Compound 10
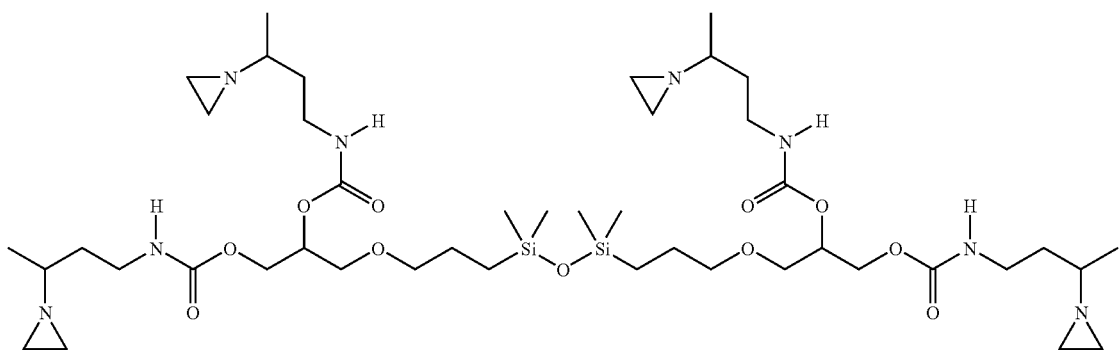

M=959; Functionality=4; (EW2)=240;
Compound 11
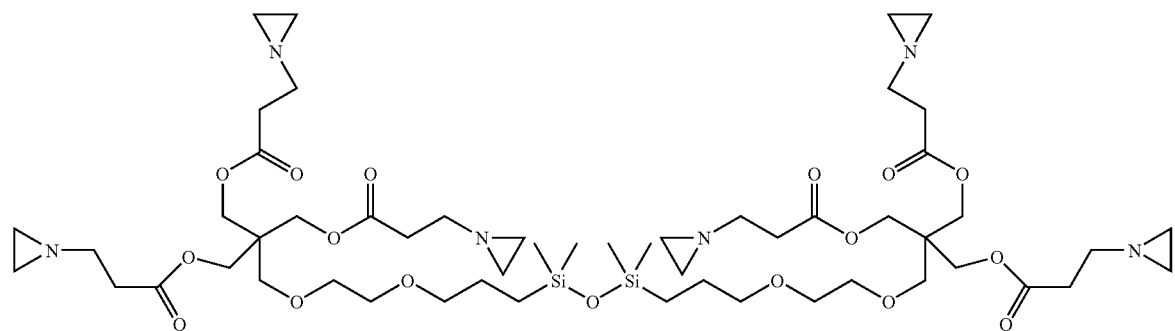
M=1158; Functionality=6; (EW2)=193
Compound 12
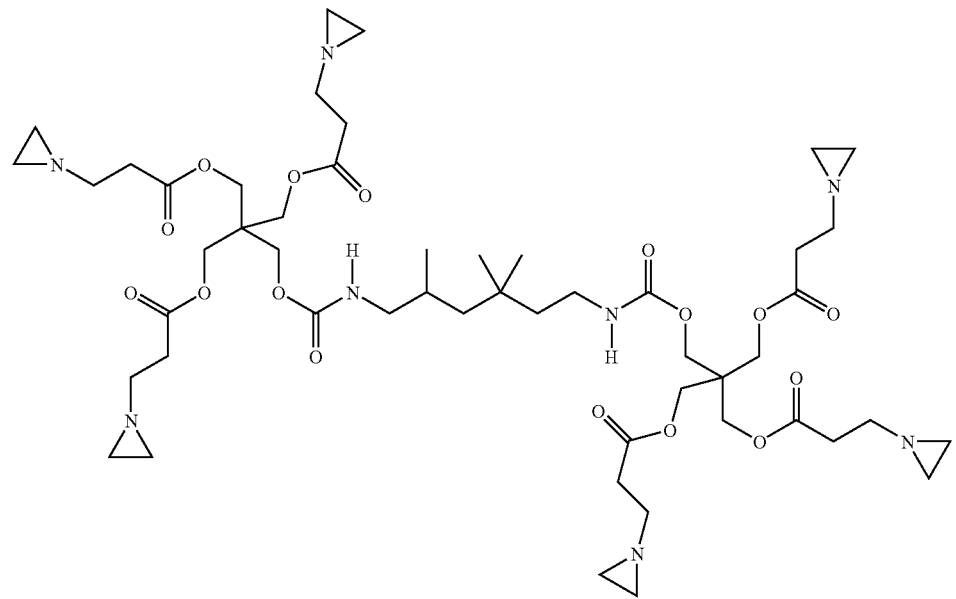

M=1065; Functionality=6; (EW2)=178
Compound 13

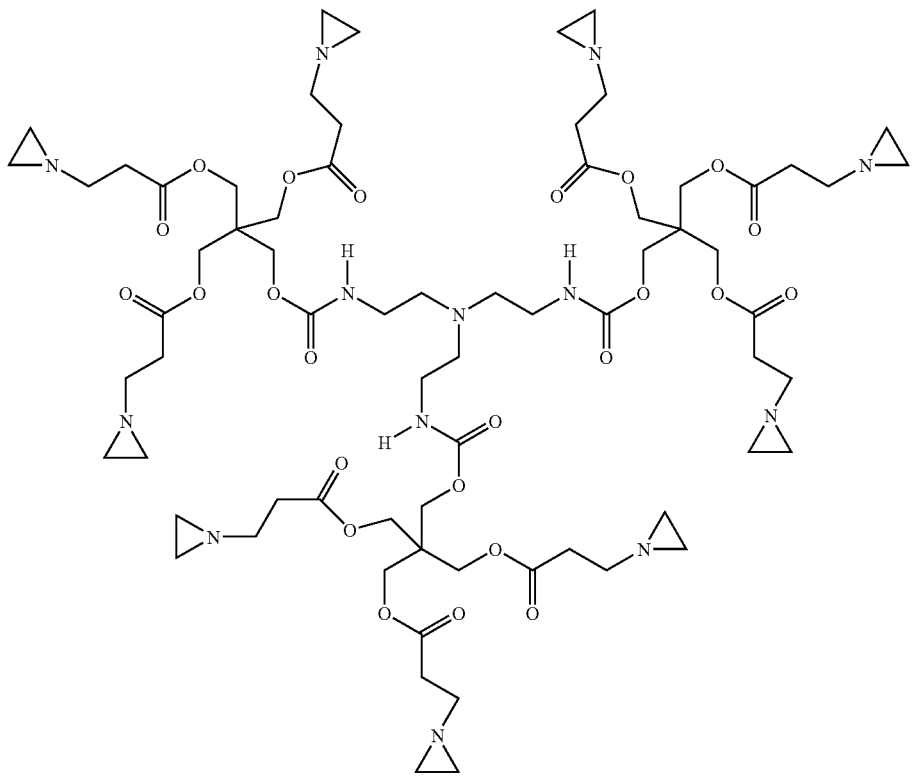

M=1507; Functionality=9; (EW2)=167
Compound 14

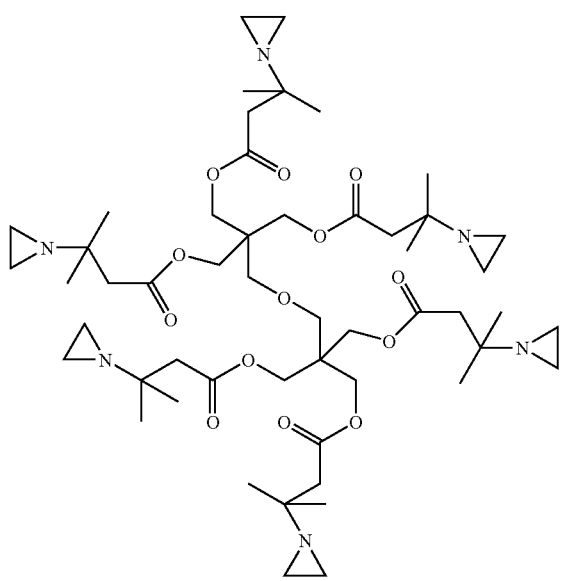

M=1005; Functionality=6; (EW2)=168

The curable composition of the invention also comprises an initiator as component (C) being able to start curing of the composition. Useful initiators are e.g. sulfonium salts, especially alkyl sulfonium salts or sulfonium salts derived from glutaconic acid. Those and others are described e.g. in EP application number 05016531.5 or U.S. Pat. No. 4,167,618, the content of which in regard to initiators is explicitly mentioned and herewith incorporated by reference.

The initiator can be used in an amount of at least about 1 wt-% or at least about 2 wt-% or at least about 3 wt-%.

The initiator can be used up to an amount of at least about 30 wt-% or at least about 20 wt-% or at least about 10 wt-%.

In addition the curable composition of the invention may comprise filler(s) as optional component (D) and/or additive(s) as optional component (E).

A wide variety of inorganic, especially hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4 to 6 μm); amorphous silicone dioxides, such as a diatomaceous earth (4 to 7 μm); and silanated fumed silica, such as Cab-o-Sil TS-530 (160-240 $m^2/g$), manufactured by Cabot Corporation. Varying the sizes and surface areas of the foregoing materials enables one to control the viscosity and thixotropicity of the uncured as well as the physical properties of the cured compositions. Some or all of the foregoing hydrophobic fillers may be surface treated with one or more silanating agents, as known to those of ordinary skill in the art. Such silanating may be accomplished, e.g., using known halogenated silanes or silazides. Some useful functionalized silicas are commercially available, e.g. products sold under the brands Aerosil™ (Degussa) or HDKH™ (Wacker).

Among the fillers which can be used are non-reinforcing fillers such as quartz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, glass and plastic powder. The non-reinforcing fillers can be surface treated. The surface treatment can generally be carried out with the same methods as described for the reinforcing fillers.

Suitable fillers also include reinforcing fillers such as e.g. pyrogenic or precipitated silicic acid and silica aluminium mixed oxides. The above mentioned fillers can be hydrophobized, e.g. by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than 50 μm.

A combination of reinforcing and non-reinforcing fillers can be desirable. In this respect, the quantity of reinforcing fillers may range from about 0.1 to about 15 wt.-%, in particular from about 1 to about 10 wt.-%. The difference in the named overall ranges, i.e. about 9 to about 80 wt.-%, can be accounted for by non-reinforcing fillers.

As the filler (D) is an optional component, it may not be present at all, but typically it can be present in the composition at an amount of from about 0 to about 80 wt.-%, or about 5 to about 70 wt.-%, or about 6 to about 60 wt.-% with respect to the whole composition.

Non-acidic fillers are preferred.

Besides filler (D) additives (E) can be present like dyes, pigments, thixotropic agents, flow improvers, polymeric thickeners, surfactants, odorous substances, diluting agents and/or flavourings. All kinds of known and compatible softeners and rheology modifiers like non reactive polymeric fluids or fats commonly used in commercialized impression materials can be added as well as pigments and stabilizers of any kind.

Preferred are those ingredients and additives that do not add unpleasant smell or taste. Compounds that have an unpleasant smell might be removed by thinfilm evaporation, if needed.

Suitable thixotropic agent(s) which can be added to the composition of the invention are organic compounds e.g. waxes according to the definition in Ullmanns Enzyklopädie der technischen Chemie, 4. Auflage, Verlag Chemie, Weinheim, Band 24, page 3 or triglycerides as described in U.S. Pat. No. 6,127,449. In general all organic non-water based thixotropic agents are suitable. That means that suitable thixotropic agents can alter the rheology especially of non-water based formulation.

Some of the untreated or surface treated inorganic fillers mentioned above may also contribute to the rheological properties of the formulation. Other thixotropic agents selected from the group of inorganic fillers are modified or unmodified bentonite(s), kaoline(s) and the like.

Suitable surfactant(s) are e.g. polyethers and polyether type materials with special structures such as Pluronic™, Synperonic™, Silwet™ type materials. Especially useful are substances described in U.S. Pat. No. 5,569,691 A1 the disclosure of which especially in regard to surfactants is herewith incorporated by reference.

Suitable diluting agent(s) usually do not contain reactive moieties like —SH or —COOH, primary or secondary amino groups, but may contain —OH. Liquids such as $C_{12}$-$C_{15}$ alkyl acetates, liquid derivatives of citric acid, esters of phthalic acid with branched alcohols like bis(2-ethylhexyl)phthalate or polymeric phthalates, $C_2$-$C_{18}$ bis(alkyl)esters of $C_2$-$C_6$ dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene solfonic acid amide, typical aromatic diluters like poly phenyls, dibenzyl toluene, xylyl toluene, dixylyl toluene and polymeric compounds like polyethers, polyesters, polycarbonates, polyolefines can be used. Also low molecular weight alcohols that may contain more than one OH-function like propane-1,2, diol may be used. From the group of polymeric compounds, polypropylene glycols and its derivatives are preferred.

As the additive (E) is an optional component, it may not be present at all, but typically it can be present in the composition at an amount of about 0.1 to about 50 wt.-% or in amount of about 4 to about 35 wt.-% or in amount of about 5 to about 40 wt.-% with respect to the whole composition.

If used as impression material in the dental field the additive(s) can be present in an amount in the range of about 10 to about 65%, or in the range of about 25 to about 60% with respect to the cured composition.

If used as duplicating material in the dental field the additive(s) can be present in the range of about 10 to about 90%, or in the range of about 20 to about 85% by weight with respect to the cured composition.

The composition of the invention preferably fulfills at least one of the following parameters:
  Shore hardness A (DIN 53505) of at least about 40 after 24 h or of at least about 45 or at least about 50 after 24 h.
  Tear strength (DIN 53504) of at least about 1.8 MPa or of at least about 1.9 MPa at least about 2 MPa.
  Elongation at break (DIN 53504) of at least about 150% or of at least about 200% or at least about 220%.
  Viscosity of at least about 10 Pa*s or of at least about 20 Pa*s or of at least about 40 Pa*s (measured at a shear rate of 95 1/s; 23° C.).

A useful composition according to the invention can comprise
  Component (A) in an amount of about 30 wt.-% to about 80 wt.-%, preferably in an amount of about 35 wt.-% to about 75 wt.-% or in an amount of about 40 wt.-% to about 70 wt.-%,
  Component (B) in an amount of about 0.1 wt.-% to about 20 wt.-%, preferably in an amount of about 0.5 wt.-% to about 15 wt.-% or in an amount of about 1 wt.-% to about 10 wt.-%,
  Component (C) in an amount of about 1 wt.-% to about 30 wt.-%, preferably in an amount of about 2 wt.-% to about 20 wt.-% or in an amount of about 3 wt.-% to about 10 wt.-%,
  Component (D) in an amount of about 0 wt.-% to about 80 wt.-%, preferably in an amount of about 5 wt.-% to about 70 wt.-% or in an amount of about 6 wt.-% to about 60 wt.-%,
  Component (E) in an amount of about 0 wt.-% to about 50 wt.-%, preferably in an amount of about 5 wt.-% to about 40 wt.-% or in an amount of about 4 wt.-% to about 35 wt.-%.

The invention also relates to a process of producing a composition as described in the text above comprising the step of
  mixing component (C) with components (A) and (B), and optionally with components (D) and (E),
wherein components (A) to (E) are defined as described the text above.
  The invention also relates to a kit of parts comprising
  Part I comprising component (A) and component (B) and optionally component (D) and/or component (E) and Part II comprising component (C) and optionally component (D) and/or component (E)
wherein components (A) to (E) are defined as described the text above.

The curable composition as described above can be used broadly for coating substrates, as sealing material, moulding material, for adhesively fixing substrates and/or making impressions, for modeling of objects or body parts.

The curable composition is especially useful for producing dental materials like precision impression materials, bite registration materials, duplicating materials, modelling materials, situation impression materials.

In this respect, the composition can be used e.g. for making impressions of soft and hard dental tissue. This can simply be achieved, e.g. filling the material into a dental tray and putting the tray into the mouth of a patient.

If used in the dental field, curing is preferably carried out at a temperature below about 50° C. or below about 40° C. or below about 30° C. A useful time range is within about 20 min or within about 10 min after mixing of the components for materials placed in patients mouth and cured (e.g., impression materials) and up to 45 min for materials used in the dental lab (e.g., duplicating materials, modelling materials). In other fields of use (sealing, moulding, coating, adhesively fixing), higher cure temperatures and longer setting times may be employed. Setting times in the range of about 30 min or about 1 hour can still be useful.

The material is regarded as cured, if the cured material fulfils the requirements for its use, e.g. a dental precision impression material typically fulfils the requirements for its use if it fulfils the requirements of ISO 4823:2000 (such as compatibility with gypsum, strain in compression, recovery from deformation, detail reproduction, linear dimensional change).

Especially in the dental field two further parameters might be of some importance: working time and oral setting time.

According to DIN EN ISO 4823:2000 impression materials can be classified as Type 0 (kneadable), Type 1 (high viscosity), Type 2 (medium viscosity), and Type 3 (low viscosity).

The total working time at room temperature (23° C.) measured according to DIN EN ISO 4823:2000 for Impregum™ Garant L DuoSoft and Permadyne™ Garant L 2:1 (3M ESPE AG), both Type 3 regular setting polyether precision impression materials, is 3 min 40 s+15 s and 4 min±15 s, respectively.

The oral setting time is given by the manufacturer in the instructions for use. According to DIN EN ISO 4823:2000 the elastomeric property recovery from deformation of the vulcanized material have to reach values of >96.5% within the recommended oral setting time. In addition according to DIN EN ISO 4823:2000 the elastomeric property strain in compression of the vulcanized material has to come up to a value within the range of 0.8 to 20.0% for Type 0 and Type 1 materials and in the range of 2.0 to 20.0% for Type 2 and Type 3 materials, respectively within the recommended oral setting time.

If the composition is to be used as dental impression material, appropriate working times are in a range of about 20 s to about 7 min or about 30 s to about 6 min at room temperature (23° C.) For impression materials oral setting times should be as short as possible. Suitable oral setting times are $\leq$ about 6 min or $\leq$ about 5 min.

If used in the dental field, the composition can be applied using e.g. the following steps:
providing the components of the composition,
mixing the components,
applying the composition to a surface,
letting the composition set.

The surface can be the surface of soft or hard oral tissue, the surface of an impression material, preferably of a cured impression material, the surface of a crown or the surface of a model of a tooth stump.

The invention also relates to a method of use of component (B) as described in the text above for increasing the tear strength and/or elongation at break of a polyether containing composition. This can be achieved by adding component (B) to the other components of the composition.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis and all water is deionized water.

Test Methods
Viscosity

Viscosity was measured using a common rheometer (Physica MCR 300) and recorded at three different shear rates (20 1/s, 50 1/s, 95 1/s) (23° C., plate-plate geometry, diameter 20 mm, gap 0.2 mm).

Tensile Strength (Mpa), Tear Strength and Elongation at Break (%)

Tensile strength, Tear Strength and Elongation at break were measure according to Deutsche Industrie Norm (DIN) or European Norm (EN) Method # 53504 (geometry S2, 200 mm/min) using Universalprüfmaschine Zwick Z020 (Zwick GmbH &Co, Ulm, Germany).

Shore A Hardness (after 24 Hours)

Shore A hardness was measured according to Deutsche Industrie Norm (DIN) Method #53505. The curable compositions were allowed to cure for 24 hours at 23° C. and ambient humidity before the hardness was measured.

Synthesis of Crosslinker Compounds
Aziridino-Derivative of Ethoxylated Pentaerythrole (Crosslinker Compound 1)

99.36 g ethoxylated pentaerythrole (0.5 Equivalent OH, 15 Mole EO per pentaerythrole molecule, Aldrich) were dissolved in the same amount of toluene. This solution was added to a stirred suspension of 81.08 g carbonyldiimidazole (CDI) (0.5 mole, purity ~97%, FLUKA) at 37° C. in 1 l toluene within 45 minutes. After additional 12 hours of stirring at 37° C. the reaction mixture was cooled to 23° C. 62.8 g 3-(ethylenimino)-butylamin (0.55 mole, Bp.: 50° C./10 Torr, p=0.8780 g/ml) (made from 3-(ethylenimino)-butyronitrile (CAS: 4078-19-7 by hydrogenation) were added in one portion and the reaction mixture was stirred at 23° C. for another 48 h. The reaction mixture was filtrated, evaporated from solvent and imidazole was stripped of by repeated thin film evaporation. Crosslinker compound 1 was isolated as a clear viscous liquid of 43 Pa*s.

Aziridino-Derivative of Propoxylated Pentaerythrole (Crosslinker Compound 3)

403.5 g propoxylated pentaerythrole (0.5 Equivalent OH, 67 Mole PO per pentaerythrole molecule, Fa. Boehme, Geretsried, Germany) were added to a stirred suspension of 81.08 g carbonyldiimidazole (CDI) (0.5 mole, purity ~97%, FLUKA) at 39° C. in 1 l methyl-tert.-butyl ether within 60 minutes, whereupon temperature rose to 46° C. After additional 4 hours of stirring at 40° C. 58.2 g 3-(ethylenimino)-butylamin (0.51 mole, Bp.: 50° C./10 Torr, p=0.8780 g/ml)

(made from 3-(ethylenimino)-butyronitrile (CAS: 4078-19-7 by hydrogenation) were added within 15 min and the reaction mixture was stirred at 23° C. for another 48 h. The reaction mixture was filtrated, evaporated from solvent and imidazole was stripped of by repeated thin film evaporation. Crosslinker compound 3 was isolated as a clear viscous liquid of 1.8 Pa*s.

Multifunctional Aziridine-Derivative Based on Cyclosiloxanes (Crosslinker Compound 4)

225.9 g of a mixture of 2-hydroxy-ethoxy-propyl-(methyl)-cyclosiloxanes $(HOCH_2CH_2OCH_2CH_2CH_2(Me)SiO)_x$ with x predominately being within the range of about 4 to about 6 (available through hydrosilation of 2-Allyloxyethanole to hydridocyclosiloxanes) (1.36 Equivalent OH; viscosity: 0.9 Pa*s, $n^D_{20}=1.4664$) were dissolved in 500 ml THF and stirred under nitrogen at 0° C. 220.4 g carbonyldiimidazole (CDI) (1.36 mole, purity ~97%, FLUKA) were added in one portion, whereupon temperature rose to 30° C. The reaction mixture was stirred at 0° C. overnight and at 23° C. for another two days. The reaction mixture was cooled to 0° C. again and 170.8 g 3-(ethylenimino)-butylamin (1.496 mole) were added within 10 minutes. The temperature rose to 50° C. while cooling. After stirring at room temperature for 2 days, imidazole was extracted with water and the solvent was evaporated. 347.6 g of crosslinker compound 4 were isolated as a highly viscous slightly yellow liquid, with a viscosity of 127 Pa*s and a $n^D_{20}=1.4862$.

Aziridino-Derivative of a Triglyceride (Crosslinker Compound 5)

594.0 g α,ω-polybutylmethacrylat diol (1.01 Equivalent OH; TEGO-Diol BD-1000, Tego Chemie Service GmbH) was dissolved in 800 ml cyclohexane at 23° C. 172.0 g CDI (1.061 mole) were added while stirring in one portion and the solution cleared up. Stirring was continued for further 24 h at 23° C. 126.9 g 3-(ethylenimino)-butylamine (1.11 mole) were added within 10 minutes at 43° C. and the solution was stirred for another 16 h. Imidazole was removed by extraction with water. Thereafter the reaction mixture was dried with $Na_2SO_4$ and the solvent was evaporated. Crosslinker compound 5 remained as a highly viscous resin with a viscosity of 1400 Pa*s and a $n^D_{20}=1.4880$.

Aziridino-Derivative of a Triglyceride (Crosslinker Compound 6)

100 g of a OH-functional triglyceride (0.326 Equivalent OH; Ligalub 9 GE-H, Peter Greven Fettchemie, OHZ=155 mg KOH/g; CAS [8001-78-3]) was dissolved in 750 ml toluene at 55° C. 52.86 g CDI were added while stirring in one portion while temperature rose to 58° C. and the solution cleared up. Stirring was continued for further 4 h at 55° C. 42.8 g 3-(ethylenimino)-butylamin (0.375 mole) were added within 10 minutes at 55° C. and the solution was stirred for another 12 h. Imidazole was removed by extraction with water. Thereafter the reaction mixture was dried with $Na_2SO_4$ and the solvent was evaporated. Crosslinker compound 6 remained as off-white semi-solid residue.

Multifunctional Aziridine-Derivative Based on Linear Siloxanes (Crosslinker Compound 7)

133.3 g of a mixture of (2-hydroxy-ethoxy-propyl-(methyl)-siloxane)-co-dimethylsiloxane $[(HOCH_2CH_2OCH_2CH_2CH_2(Me)SiO)_x\text{-co-}(Me_2SiO)_y]$ (available through hydrosilation of 2-Allyloxy-ethanole to the hydrido-(methyl)-siloxane)-co-dimethylsiloxane Crosslinker 110; Hanse Chemie M: ~6600) (1.36 Equivalent OH; viscosity: 1.7 Pa*s) were dissolved in 300 ml toluene and stirred under nitrogene at 0° C. 61.4 g carbonyldiimidazole (CDI) (0.379 mole, purity ~97%, FLUKA) were added in one portion, whereupon temperature temporarily rose to 15° C. The reaction mixture was stirred at 0° C. for 1 h and at 23° C. for another two days. The reaction mixture was cooled to 0° C. again and 170.8 g—(ethylenimino)-butylamin (1.496 mole) were added within 10 minutes. The temperature rose to 30° C. while cooling. After stirring at room temperature for 2 days, imidazole was extracted with water and the solvent was evaporated. 132.6 g of crosslinker compound 7 were isolated as a viscous yellow liquid, with. a viscosity of 6.7 Pa*s and a $n^D_{20}=1.4566$.

The following formulations were prepared:

Base Paste 1

| | |
|---|---|
| 53.0% | difunctional aziridino polyether (polyether back bone is a copolymer EO/THF with a molecular weight of 6000) |
| 15.0% | fat (trisacylic ester of glycerine) |
| 9.0% | dibenzyl toluene |
| 0.5% | lauryl imidazole |
| 6.5% | diatomaceous earth |
| 16.0% | unreactive polyether (polyether back bone is a copolymer EO/THF with a molecular weight of 6000) |

Catalyst Paste 1

| | |
|---|---|
| 19.5% | sulfonium salt tetafluoroborate |
| 41.0% | acetyl tributyl citrate |
| 3.5% | surfactant (copolymer EO/PO) |
| 12.0% | diatomaceous earth |
| 24.0% | highly dispersed silica, surface treated |

In all formulations using Base Paste 1 and Catalyst Paste 1, the catalyst paste and the base paste were mixed together in a volume ratio of 1:5 (equivalent to the ratio by weight 1.00 g base paste and 0.24 g catalyst paste). The dental impression material was prepared by mixing 1.00 g of base paste with 0.24 g of catalyst paste using a spatula. The resulting mass was allowed to cure at room temperature for 24 hours before the Shore A hardness was measured.

(A) Adding Different Highly Functional Crosslinkers to the Formulation

Base Paste 1 was reacted with the Catalyst Paste 1 (Table 1, Entry 0, Comparative Example).

In the following experiments parts of the unreactive polyether in Base Paste 1 was exchanged against crosslinker compounds. The formulas of the crosslinker compounds used are described in the specification above.

Whereas in the base paste without crosslinker the concentration of aziridino groups is about $1.726 * 10^{-2}$ mol per 100 g in all of the altered formulation, the concentration of aziridino groups was attuned to $2.510 * 10^{-2}$ mol per 100 g base paste by exchanging the same amount of unreactive polyether.

The amount of lauryl imidazole was altered to keep an approximate ratio of aziridine groups:lauryl imidazole of about 1.00 to about 0.1. To assure that in all experiments the same ratio of aziridino groups:sulfonium salt tetafluoroborate is used, the amount of sulfonium salt tetafluoroborate in Catalyst Paste 1 was adapted to 28.3 g by exchanging the same amount of acetyl tributyl citrate. The altered base pastes were reacted with the altered catalyst pastes.

Table 1 describes the effect the addition of crosslinkers has on the value of tear strength and elongation at break. The naming of the crosslinker as 1, 3, 4, . . . corresponds to the numbering of the crosslinkers in the text above in regard to formulas and synthesis.

TABLE 1

| Entry | Cross-linker | Aziridino groups in 100 g base paste | Shore Hardness A after 24 h | Viscosity Base Paste [Pas] 20 1/s | Viscosity Base Paste [Pas] 50 1/s | Viscosity Base Paste [Pas] 95 1/s | Tensile Test DIN 53504 (Geometry S 2) Tear Strength [MPa] | Tensile Test DIN 53504 (Geometry S 2) Elongation [%] |
|---|---|---|---|---|---|---|---|---|
| 0 | — | $1.726 \times 10^{-2}$ mol | 45 | 136 | 101 | 81 | $1.49 \pm 0.18$ | $223 \pm 43$ |
| 1 | 1 | $2.510 \times 10^{-2}$ mol | 46 | 181 | 113 | 81 | $2.10 \pm 0.17$ | $316 \pm 36$ |
| 2 | 3 | $2.510 \times 10^{-2}$ mol | 54 | 84 | 65 | 53 | $1.99 \pm 0.23$ | $200 \pm 37$ |
| 3 | 4 | $2.510 \times 10^{-2}$ mol | 52 | 111 | 81 | 65 | $2.27 \pm 0.13$ | $260 \pm 22$ |
| 4 | 5 | $2.510 \times 10^{-2}$ mol | 53 | 122 | 90 | 70 | $2.45 \pm 0.28$ | $281 \pm 39$ |
| 5 | 6 | $2.510 \times 10^{-2}$ mol | 56 | 73 | 62 | 56 | $2.28 \pm 0.14$ | $247 \pm 17$ |
| 6 | 7 | $2.510 \times 10^{-2}$ mol | 58 | 133 | 94 | 73 | $2.86 \pm 0.16$ | $289 \pm 26$ |

(B) Varying the Concentration of the Highly Functionalized Crosslinkers

In the following experiments parts of the unreactive polyether in Base Paste 1 was exchanged against the same amount of crosslinker. Whereas in the base paste without crosslinker the concentration of aziridino groups is about $1.726 \times 10^{-2}$ mol per 100 g, in the altered formulation the concentration of aziridino groups was attuned to about $2.510 \times 10^{-2}$ mol and about $3.269 \times 10^2$ mol per 100 g base paste, respectively. The amount of lauryl imidazole was also altered to keep an approximate ration of aziridine groups: lauryl imidazole of about 1.00 to about 0.1.

The resulting formulations were reacted with altered Catalyst Pastes 1. Catalyst pastes were altered in the same manner as described in (A) (Table 1, Entries 1-6) assuring always the same ratio of aziridino groups:sulfonium salt tetra-fluoroborate.

Table 2 and Table 3 show the data for exchanging different amounts of unreactive polyether in Base Paste 1 against crosslinkers 1 and 4.

Table 2

TABLE 2 using crosslinker 1 (Entry 1: 3.81%, Entry 7: 7.50% by weight)

| Entry | Cross-linker | Aziridino groups in 100 g base paste | Shore Hardness A after 24 h | Viscosity Base Paste [Pas] 20 1/s | Viscosity Base Paste [Pas] 50 1/s | Viscosity Base Paste [Pas] 95 1/s | Tensile Test DIN 53504 (Geometry S 2) Tear Strength [MPa] | Tensile Test DIN 53504 (Geometry S 2) Elongation [%] |
|---|---|---|---|---|---|---|---|---|
| 0 | — | $1.726 \, 10^{-2}$ mol | 45 | 136 | 101 | 81 | $1.49 + 0.18$ | $223 \pm 43$ |
| 1 | 1 | $2.510 \, 10^{-2}$ mol | 46 | 181 | 113 | 81 | $2.10 \pm 0.17$ | $316 \pm 36$ |
| 7 | 1 | $3.269 \, 10^{-2}$ mol | 50 | 129 | 97 | 78 | $2.42 \pm 0.07$ | $338 \pm 16$ |

Table 3

TABLE 3 using crosslinker 4 (Entry 3: 2.85%, Entry 8: 5.00%, Entry 9: 7.00%)

| Entry | Cross-linker | Aziridino groups in 100 g base paste | Shore Hardness A after 24 h | Viscosity Base Paste [Pas] 20 1/s | Viscosity Base Paste [Pas] 50 1/s | Viscosity Base Paste [Pas] 95 1/s | Tensile Test DIN 53504 (Geometry S 2) Tear Strength [MPa] | Tensile Test DIN 53504 (Geometry S 2) Elongation [%] |
|---|---|---|---|---|---|---|---|---|
| 0 | — | $1.726 \times 10^{-2}$ mol | 45 | 136 | 101 | 81 | $1.49 \pm 0.18$ | $223 \pm 43$ |
| 3 | 4 | $2.510 \times 10^{-2}$ mol | 52 | 111 | 81 | 65 | $2.27 + 0.13$ | $260 \pm 22$ |
| 8 | 4 | $3.103 \times 10^{-2}$ mol | 53 | 105 | 80 | 66 | $2.75 \pm 0.20$ | $286 \pm 24$ |
| 9 | 4 | $3.654 \times 10^{-2}$ mol | 51 | 96 | 76 | 64 | $2.78 \pm 0.16$ | $317 \pm 20$ |

The invention claimed is:

1. A dental composition comprising:
   a) a prepolymer as component (A), wherein the prepolymer comprises aziridino groups and is characterized by an equivalent weight EW1, a crosslinker as component (B), wherein the crosslinker has a molecular structure being different from the molecular structure of the prepolymer and comprises aziridino groups and is characterized by an equivalent weight EW2, and wherein the crosslinker has one of the following structures:

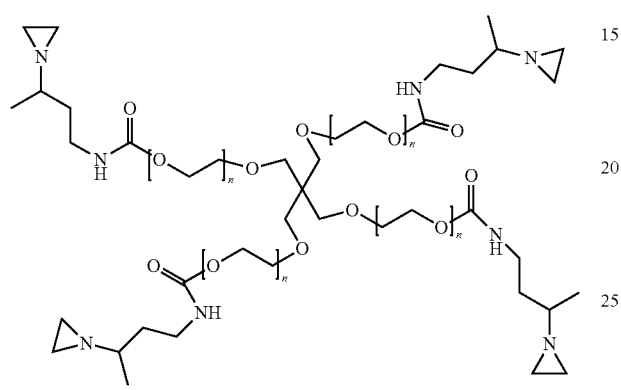

n = 2 - 30

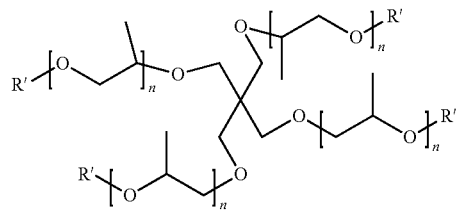

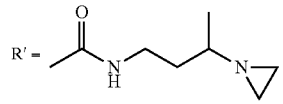

n = 2 - 30

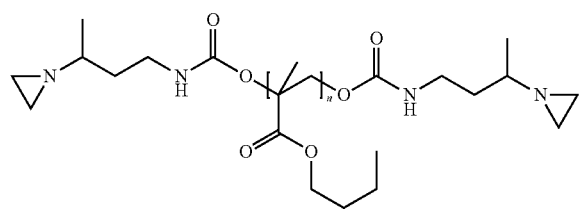

n = 8 - 20

-continued

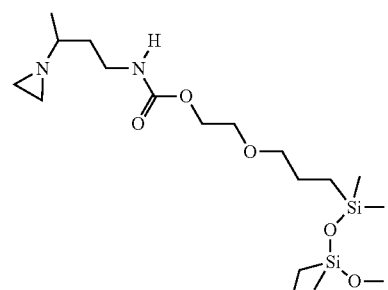

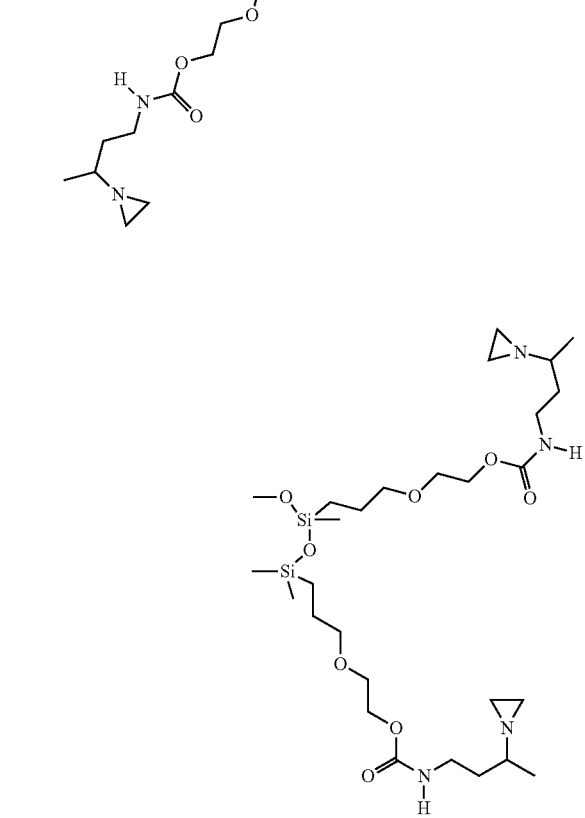

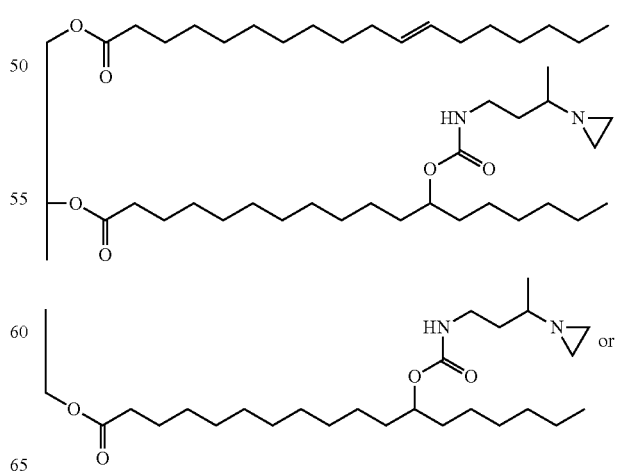

or

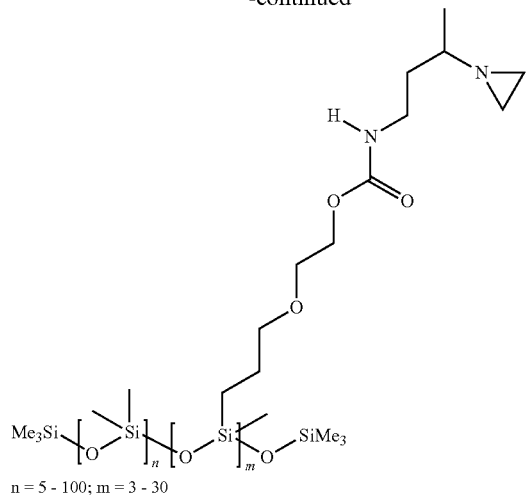

n = 5 - 100; m = 3 - 30 b) an initiator as component (C) being able to start curing of the composition,
c) optionally filler(s) as component (D) and
d) optionally additive(s) as component (E), wherein equivalent weight is defined as (molecular mass of the molecule)/(number of aziridino groups present in the molecule) and wherein EW1 >EW2 and
wherein the prepolymer has a molecular weight (Mn) within the range of about 3,000 to about 12,000 and the crosslinker has a molecular weight (Mn) within the range of about 500 to about 5,000.

2. The composition according to claim 1 fulfilling at least one of the following parameters after curing:
  e) Shore hardness A (DIN 53505) of at least 46 after 24h,
  f) Tear strength (DIN 53504) of at least 1,6 MPa,
  g) Elongation at break (DIN 53504) of at least 150%.

3. The composition according to claim 1, comprising
  h) Component (A) in an amount of about 10 wt.-% to about 90 wt.-%,
  i) Component (B) in an amount of about 5 wt.-% to about 50 wt.-%,
  j) Component (C) in an amount of about 1 wt.-% to about 30 wt.-%,
  k) Component (D) in an amount of about 0 wt.-% to about 80 wt.-%,
  l) Component (E) in an amount of about 0 wt.-% to about 80 wt.-%.

4. The composition according to claim 1, wherein the prepolymer is characterized by at least one of the following features:

m) molecular weight (Mn) in the range of about 3,000 to about 30,000,
  n) molecular structure of the backbone: linear,
  o) number of aziridino groups: at least 2,
  p) equivalent weight (EW1) in the range of about 1,000 to about 6,000.

5. The composition according to claim 1, wherein the prepolymer comprises polyether, polyurethane and/or polyester moieties.

6. The composition according to claim 1, wherein the prepolymer does not contain silicone functions.

7. The composition according to claim 1, wherein the crosslinker is characterized by at least one of the following features:
  a. molecular weight (M, Mn) in the range of about 200 to about 10,000,
  b. molecular structure of the backbone: branched,
  c. number of aziridino groups: at least 2,
  d. equivalent weight (EW2) in the range of about 100 to about 1,600.

8. The composition according to claim 1, wherein the filler(s) is/are selected from the groups consisting of reinforcing and non-reinforcing fillers.

9. The composition according to claim 1 wherein the additive(s) is/are selected from the groups consisting of dyes, pigments, thixotropic agents, flow improvers, polymeric thickeners, surfactants, odorous substances, diluting agents and flavourings.

10. A kit of parts to be used in the dental field comprising
  Part I comprising component (A) and component (B) and optionally component (D) and/or component (E) and
  Part II comprising component (C) and optionally component (D) and/or component (E),
wherein components (A) to (E) are defined as described in claim 1 above.

11. A process of producing a dental composition as described in claim 1, the method comprising the steps of:
  mixing component (C) with components (A) and (B), and optionally with components (D) and (E),
  wherein components (A) to (E) are defined as described in claim 1 above.

12. A method of using the dental composition as described in claim 1 for making impressions or producing a dental material.

13. The method according to claim 12, wherein the dental material is a precision impression material, situation impression material, bite registration material, duplicating material or modelling material.

* * * * *

UNITED STATES PATENT AND TRADEMARK OFFICE
CERTIFICATE OF CORRECTION

PATENT NO.      : 8,022,113 B2
APPLICATION NO. : 12/278983
DATED           : September 20, 2011
INVENTOR(S)     : Thomas Klettke It is certified that error appears in the above-identified patent and that said Letters Patent is hereby corrected as shown below:

Column 3
Lines 30-33        Delete "The lower the.........................component (B)." and insert the same on Col. 3, Line 29, after "molecule" as a continuation of the same paragraph.
Line 45            Delete "know" and insert -- known --, therefor.

Column 5
Line 12            Delete "prepolmyer" and insert -- prepolymer --, therefor.

Column 7
Line 22            Delete "innositol," and insert -- inositol, --, therefor.
Line 23            Delete "etylene" and insert -- ethylene --, therefor.

Column 10
Lines 5-15

Delete " 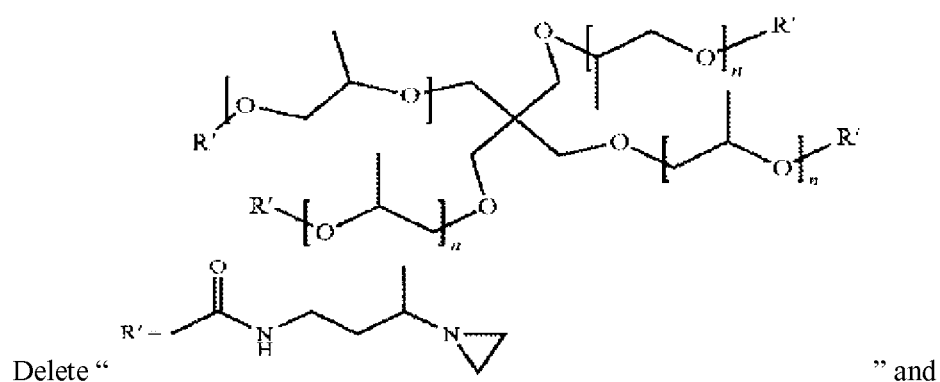 " and

Signed and Sealed this
Tenth Day of April, 2012

David J. Kappos
*Director of the United States Patent and Trademark Office*

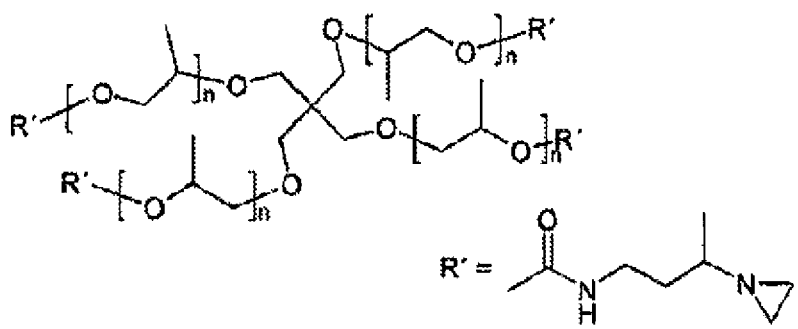

insert --                                           --, therefor.

Column 20
Line 3            Delete "solfonic" and insert -- sulfonic --, therefor.
Line 3            Delete "solfonic" and insert -- sulfonic --, therefor.

Column 22
Line 28          Delete "(Mpa)," and insert -- (MPa), --, therefor.
Line 47          Delete "11" and insert -- 1l--, therefor.
Line 64          Delete "11" and insert -- 1l--, therefor.
Line 64          Delete "tert.-butyl" and insert -- tert-butyl --, therefor.

Claim 23
Line 29          Delete "polybutylmethacrylat" and insert -- polybutylmethacrylate --, therefor.

Claim 24
Line 16          Delete "trisacylic" and insert -- trisacrylic --, therefor.
Line 26          Delete "tetafluoroborate" and insert -- tetrafluoroborate --, therefor.
Line 58          Delete "tetafluoroborate" and insert -- tetrafluoroborate --, therefor.
Line 59          Delete "tetafluoroborate" and insert -- tetrafluoroborate --, therefor.

Column 25
Line 25          Delete "102" and insert -- $10^{-2}$ --, therefor.

Column 28
Lines 50-65
Claim 1, delete " 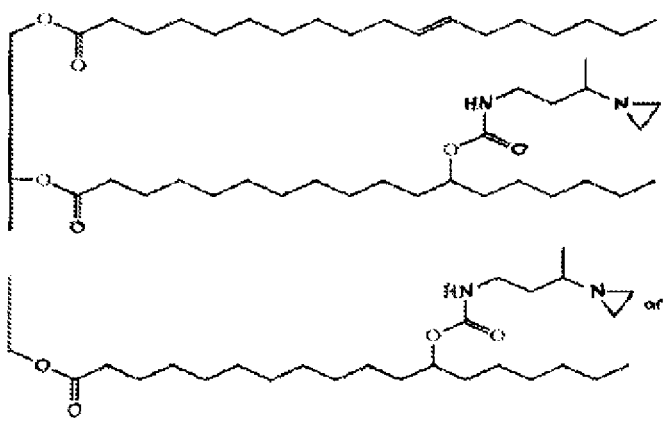 " and
insert -- 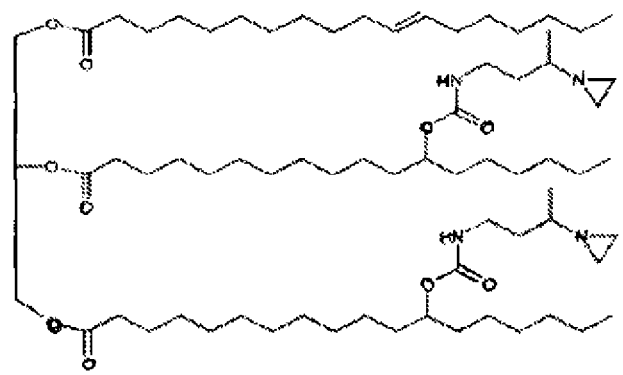 --, therefor.
Column 29
Line 36    In Claim 2, delete "1,6" and insert -- 1.6 --, therefor.